(12) United States Patent
Koo et al.

(10) Patent No.: US 7,427,513 B2
(45) Date of Patent: *Sep. 23, 2008

(54) SURFACE MODIFICATION OF METALS FOR BIOMOLECULE DETECTION USING SURFACE ENHANCED RAMAN SCATTERING (SERS)

(75) Inventors: Tae-Woong Koo, Cupertino, CA (US); Selena Chan, San Jose, CA (US); Xing Su, Cupertino, CA (US); Jingwu Zhang, Santa Clara, CA (US); Lei Sun, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 440 days.

This patent is subject to a terminal disclaimer.

(21) Appl. No.: 11/133,707

(22) Filed: May 19, 2005

(65) Prior Publication Data

US 2005/0221508 A1    Oct. 6, 2005

Related U.S. Application Data

(62) Division of application No. 10/814,695, filed on Mar. 30, 2004, now Pat. No. 7,351,591.

(51) Int. Cl.
*G01N 33/553* (2006.01)

(52) U.S. Cl. .......................... 436/525; 436/518; 436/524; 435/283.1; 435/287.1; 435/287.2; 435/288.7

(58) Field of Classification Search .................. 436/518, 436/524, 525, 532; 422/82.01, 82.05; 435/4, 435/7.1, 174, 287.2, 288.7; 516/1, 9, 37

See application file for complete search history.

(56) References Cited

U.S. PATENT DOCUMENTS

| | | | |
|---|---|---|---|
| 5,306,403 A | 4/1994 | Vo-Dinh | |
| 5,376,556 A | 12/1994 | Tarcha et al. | |
| 5,384,265 A | 1/1995 | Kidwell et al. | |
| 5,521,287 A | 5/1996 | Ohmura et al. | |
| 5,736,624 A | 4/1998 | Bieniarz et al. | |
| 5,866,430 A | 2/1999 | Grow | |
| 5,945,293 A | 8/1999 | Siiman et al. | |
| 6,002,471 A | 12/1999 | Quake | |
| 6,127,120 A | 10/2000 | Graham et al. | |
| 6,149,868 A | 11/2000 | Natan et al. | |
| 6,174,677 B1 | 1/2001 | Vo-Dinh | |
| 6,514,767 B1 | 2/2003 | Natan ......................... 436/166 | |

(Continued)

OTHER PUBLICATIONS

Doering, et al., "Spectroscopic Tags Using Dye-Embedded Nanoparticles and Surface-Enhanced Raman Scattering", *Analytical Chemistry*, :5-9, ((2003).

(Continued)

*Primary Examiner*—Long V. Le
*Assistant Examiner*—Melanie J Yu
(74) *Attorney, Agent, or Firm*—Darby & Darby PC

(57) ABSTRACT

The present invention is based on the discovery that the methods described herein for the production of metallic colloids result in colloids exhibiting increased signal enhancement and reproducibility for the SERS detection of biomolecules. Thus, using the methods of the invention, a wide variety of biomolecules can be detected with a greater sensitivity and reliability.

9 Claims, 3 Drawing Sheets

U.S. PATENT DOCUMENTS

| | | |
|---|---|---|
| 6,540,970 B1 | 4/2003 | Strohmaier et al. |
| 6,699,507 B1 | 3/2004 | Albrecht et al. |
| 6,699,724 B1 | 3/2004 | West et al. |
| 6,716,480 B2 | 4/2004 | Yukinobu et al. |
| 6,770,488 B1 | 8/2004 | Carron et al. |
| 6,875,465 B2 | 4/2005 | Bishop et al. |
| 2001/0014717 A1 | 8/2001 | Hossainy et al. |
| 2003/0199653 A1 | 10/2003 | McCormick et al. |
| 2003/0211488 A1 | 11/2003 | Mirkin et al. |
| 2004/0234958 A1 | 11/2004 | Smith et al. |
| 2004/0250750 A1 | 12/2004 | Reda et al. |

OTHER PUBLICATIONS

Lee, et al., "Adsorption and Surface-Enhanced Raman of Dyes on Silver and Gold Sols", *J. Phys. Chem.* 86:3391-3395, (1982).

Mulvaney, et al., "Glass-Coated, Analyte-Tagged Nanoparticles: A New Tagging System Based on *Detection* with Surface-Enhanced Raman Scattering", *Am Chem Soc.* 19:4784-4790 (2003).

Nie, et al., "Probing Single Molecules and Single Nanoparticles by Surface-Enhanced Raman Scattering", *Sci.* 275:1102-1106, (1997).

SURFACE MODIFICATION OF METALS FOR BIOMOLECULE DETECTION USING SURFACE ENHANCED RAMAN SCATTERING (SERS)

CROSS REFERENCE TO RELATED APPLICATIONS

This application is a divisional application of U.S. Ser. No. 10/814,695, filed Mar. 30, 2004, now U.S. Pat. No. 7,351,591. The disclosure of the prior application is considered part of and is incorporated by reference in the disclosure of this application.

BACKGROUND OF THE INVENTION

1. Field of the Invention

The invention relates generally to surface modified metallic particles that include organic molecules attached to the surface of metallic colloids, and more specifically to the use of such surface modified particles in analyte detection by surface-enhanced Raman spectroscopy.

2. Background Information

The ability to detect and identify trace quantities of analytes has become increasingly important in virtually every scientific discipline, ranging from part per billion analyses of pollutants in sub-surface water to analysis of cancer treatment drugs in blood serum. Raman spectroscopy is one analytical technique that provides rich optical-spectral information, and surface-enhanced Raman spectroscopy (SERS) has proven to be one of the most sensitive methods for performing quantitative and qualitative analyses. A Raman spectrum, similar to an infrared spectrum, consists of a wavelength distribution of bands corresponding to molecular vibrations specific to the sample being analyzed analyte). In the practice of Raman spectroscopy, the beam from a light source, generally a laser, is focused upon the sample to thereby generate inelastically scattered radiation, which is optically collected and directed into a wavelength-dispersive spectrometer in which a detector converts the energy of impinging photons to electrical signal intensity.

Among many analytical techniques that can be used for chemical structure analysis, Raman spectroscopy is attractive for its capability in providing rich structure information from a small optically-focused area or detection cavity. Compared to a fluorescent spectrum that normally has a single peak with half peak width of tens of nanometers (quantum dots) to hundreds of nanometers (fluorescent dyes), a Raman spectrum has multiple bonding-structure-related peaks with half peak width of as small as a few nanometers. Furthermore, surface enhanced Raman scattering (SERS) techniques make it possible to obtain a $10^6$ to $10^{14}$ fold Raman signal enhancement, and may even allow for single molecule detection sensitivity. Such huge enhancement factors are attributed primarily to enhanced electromagnetic fields on curved surfaces of coinage metals. Such enhancement factors have also been observed on sharp edges and at the junctions between aggregates. Although the electromagnetic enhancement (EME) has been shown to be related to the roughness of metal surfaces or particle size when individual metal colloids are used, SERS is most effectively detected from aggregated colloids. It is known that chemical enhancement can also be obtained by placing molecules in a close proximity to the surface in certain orientations. Due to the rich spectral information and sensitivity, Raman signatures have been used as probe identifiers to detect a few attomoles of molecules when SERS method was used to burst the signals of specifically immobilized Raman label molecules, which in fact are the direct analytes of the SERS reaction. The method of attaching metal particles to Raman-label-coated metal particles to obtain SERS-active complexes has also been studied. A recent study demonstrated that SERS signal can be generated after attaching thiol containing dyes to gold particle followed silica coating.

Unfortunately, reliable methods for producing metallic colloids with consistent SERS performance have not yet been developed. In addition, there is a limited number of biomolecules (such as, for example, proteins) that adsorb to metallic surfaces to generate a SERS signal, and even for proteins that do adsorb, the signal intensity is low. Thus, a need exists for methods for producing metallic colloids with consistent SERS performance for detection of biomolecules such as proteins. In addition, there exists a need for methods for producing metallic colloids that are biomolecule specific.

DETAILED DESCRIPTION OF THE INVENTION

Figure 1:
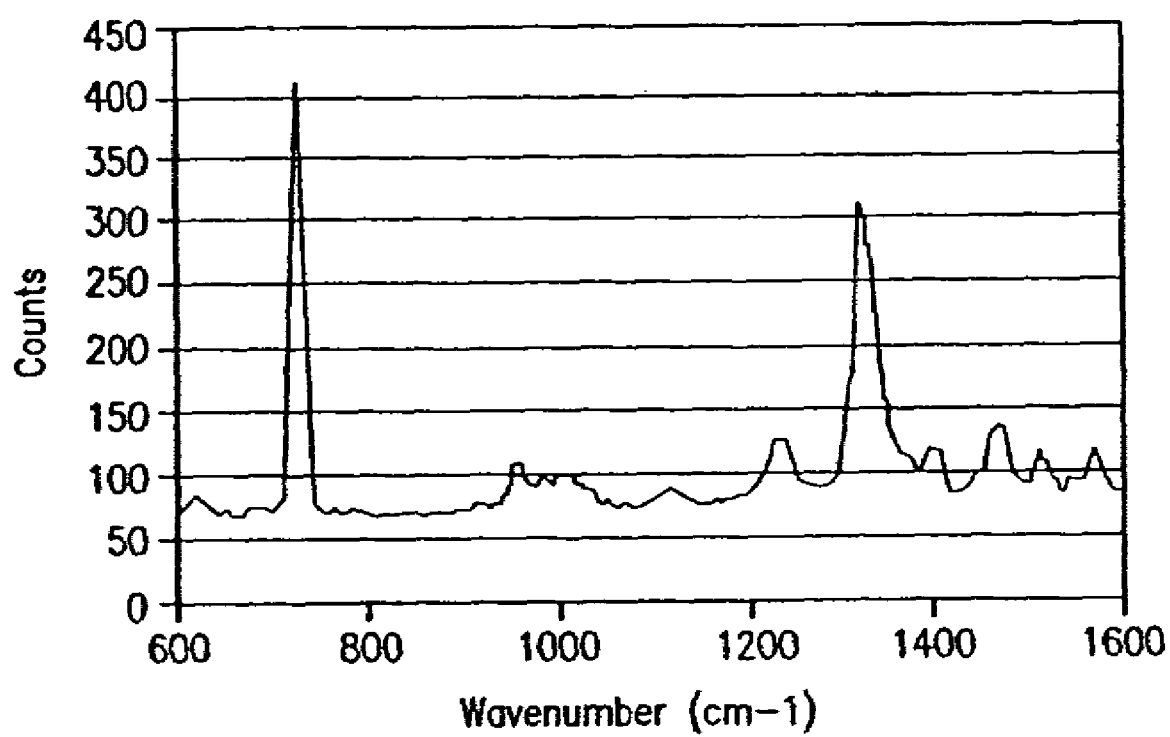
FIG. 1 illustrates a typical Surface Enhanced Raman Spectrum of dAMP obtained using the metallic colloids produced by the methods of the invention.

The present invention is based on the discovery that the methods described herein for the production of metal colloids result in colloids exhibiting increased signal enhancement and reproducibility for the SERS detection of biomolecules. Indeed, the surface modified metal colloids provided herein have the ability to adsorb specific target biomolecules in a specific orientation. Indeed, the colloids employed in the methods of the invention can be tailored for specific target biomolecules, for example, certain colloids can be prepared for adsorbing proteins, while other colloids can be prepared for adsorbing nucleic acids. Thus, using the methods of the invention, a wide variety of biomolecules can be detected with a greater sensitivity and reliability.

In one embodiment, there are provided methods for producing metallic colloids. Such methods can be performed, for example, by contacting metal cations with a reducing agent in aqueous solution, and heating the aqueous solution to about 95° C.; thereby producing metallic colloids. In other embodiments, the surface of the metallic colloids is modified by attaching an organic molecule to the surface of the colloids.

In another embodiment, there are provided methods for detecting a biomolecule in a sample. Such methods can be performed, for example, by modifying a metallic surface with an organic molecule having affinities for the metallic surface and for the biomolecule, contacting the modified metallic surface with the biomolecule, and detecting SERS signals emitted by the biomolecule, wherein the signals are indicative of the presence of the biomolecule.

In another embodiment, there are provided methods for detecting an analyte in a sample. Such methods can be performed, for example, by contacting a sample containing an analyte with a plurality of surface modified metallic colloids, wherein the analyte binds to the modified metallic surface, and detecting SERS signals emitted by the analyte, wherein the signals are indicative of the presence of the analyte.

In another embodiment, there are provided systems for detecting an analyte in a sample, including an array including more than one surface modified metallic colloid; a sample containing at least one analyte; a Raman spectrometer; and a computer including an algorithm for analysis of the sample.

In another embodiment, there are provided kits for labeling surface modified metallic colloids including a plurality of metallic colloids surface modified according to the methods of the invention and a biological agent.

In another embodiment, there are provided methods of identifying a microorganism. Such methods can be performed, for example, by contacting a sample suspected of containing the microorganism with an array of metallic colloids surface modified by the method of the invention; detecting SERS signals upon contacting the sample with the modified metallic colloids and associating the SERS signals from the modified metallic colloids with the identity of the microorganism.

In another embodiment, there are provided methods of identifying an analyte. Such methods can be performed, for example, by contacting a sample suspected of containing the analyte with an array of metallic colloids surface modified by the method of the invention; detecting SERS signals upon contacting the sample with the modified metallic colloids; and associating the SERS signals from the modified metallic colloids with the identity of the analyte.

In one embodiment, there are provided methods for producing metallic colloids. Such methods can be performed, for example, by contacting metal cations with a reducing agent in aqueous solution, and heating the aqueous solution to about 95° C., thereby producing metallic colloids. As used herein, the term "colloid" refers to nanometer size metal particles suspending in a liquid, usually an aqueous solution. In the methods of the invention, the metal cations and reducing agent are mixed in aqueous solution prior to heating. This method results in a 50% enhancement of SERS signals obtained from such colloids, and also results in a increase in reproducibility of 10-20% to 80-100%. Typical metals contemplated for use in the practice of the invention include, for example, silver, gold, platinum, copper, aluminum, and the like.

A variety of reducing agents are contemplated for use in the practice of the invention, such as for example, citrate, borohydride, and the like. Sodium citrate is used in certain embodiments of the invention. Typically, the metal cation and reducing agent are each present in aqueous solution at a concentration of at least about 0.5 M. After mixing the metal cation and reducing agent, the solution is heated for about 30 minutes. In some embodiments, the solution is heated for about 60 minutes. Typically, the solution is heated to about 95° C. In other embodiments, the solution is heated to about 100° C. Heating of the solution is accomplished in a variety of ways well known to those skilled in the art. In some embodiments, the heating is accomplished using a microwave oven, a convection oven, or a combination thereof.

The methods for producing metallic colloids described herein are in contrast to prior methods wherein a boiling silver nitrate solution is titrated with a sodium citrate solution. This titration method can produce only one batch of silver particles with adequate Raman enhancement to dAMP in about 10 attempts, and the other batches have low or no Raman activity at all. However, by employing the methods of the invention, an average SERS signal enhancement of 150% is observed relative to colloids prepared from the titration method.

In another embodiment of the invention, the metallic colloids produced by invention methods are modified by attaching an organic molecule to the surface of the colloids. Organic molecules contemplated for use in the practice of the invention are typically less than about 500 Dalton in molecular weight, and are bifunctional organic molecules. As used herein, "bifunctional" means that the organic molecule has a moiety that has an affinity for the metallic surface, and a moiety that has an affinity for a biomolecule. Such surface modified metallic colloids exhibit an increased ability to bind biomolecules, thereby resulting in an enhanced and reproducible SERS signal. The colloids can be used either individually, or as aggregates for binding certain biomolecules.

Organic molecules contemplated for use include molecules having any moiety that exhibits an affinity for the metals contemplated for use in the methods of the invention (i.e., silver, gold, platinum, copper, aluminum, and the like), and any moiety that exhibit affinities for biomolecules. For example, with regard to silver or gold affinity, in some embodiments, the organic molecule has a sulfur containing moiety, such as for example, thiol, disulfide, and the like. With regard to affinity for a biomolecule such as a polynucleotide, for example, the organic molecule has a carboxylic acid moiety. In certain embodiments, the organic molecule is thiomalic acid, L-cysteine diethyl ester, S-carboxymethyl-L-cysteine, cystamine, meso-2,3-dimercaptosuccinic acid, and the like. It is understood, however, that any organic molecule that meets the definition of "bifunctional", as described herein, is contemplated for use in the practice of the invention. It is also understood that the organic molecule may be attached to the metallic surface and the biomolecule either covalently, or non-covalently. Indeed, the term "affinity" is intended to encompass the entire spectrum of chemical bonding interactions, which are well-known to those skilled in the art.

This surface modification of metallic colloids provides certain advantages in SERS detection analyses. Since a wide variety of organic molecules can be used in the invention methods, the surfaces of the metallic colloids can be tailored to bind to a specific biomolecule. For example, the surfaces can be tailored to differentiate among groups of proteins based on the side chains of the individual amino acid residues found in the protein.

In other embodiments, there are provided methods for detecting a biomolecule in a sample. Such methods can be performed, for example, by modifying a metallic surface with an organic molecule having affinities for the metallic surface and for the biomolecule, contacting the modified metallic surface with the biomolecule, and detecting SERS signals emitted by the biomolecule, wherein the signals are indicative of the presence of the biomolecule.

The term "biomolecule" include antibodies, antigens, polynucleotides, oligonucleotides, receptors, ligands, and the like The term "polynucleotide" is used broadly herein to mean a sequence of deoxyribonucleotides or ribonucleotides that are linked together by a phosphodiester bond. For convenience, the term "oligonucleotide" is used herein to refer to a polynucleotide that is used as a primer or a probe. Generally, an oligonucleotide useful as a probe or primer that selectively hybridizes to a selected nucleotide sequence is at least about 10 nucleotides in length, usually at least about 15 nucleotides in length, for example between about 15 and about 50 nucleotides in length.

A polynucleotide can be RNA or can be DNA, which can be a gene or a portion thereof, a cDNA, a synthetic polydeoxyribonucleic acid sequence, or the like, and can be single stranded or double stranded, as well as a DNA/RNA hybrid. In various embodiments, a polynucleotide, including an oligonucleotide (e.g., a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide or oligonucleotide also can contain nucleotide analogs, including non-naturally occurring synthetic nucleotides or modified naturally occurring nucleotides.

The covalent bond linking the nucleotides of a polynucleotide generally is a phosphodiester bond. However, the covalent bond also can be any of numerous other bonds, including a thiodiester bond, a phosphorothioate bond, a peptide-like amide bond or any other bond known to those in the art as useful for linking nucleotides to produce synthetic polynucleotides. The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

As used herein, the term "selective hybridization" or "selectively hybridize," refers to hybridization under moderately stringent or highly stringent conditions such that a nucleotide sequence preferentially associates with a selected nucleotide sequence over unrelated nucleotide sequences to a large enough extent to be useful in identifying the selected nucleotide sequence. It will be recognized that some amount of non-specific hybridization is unavoidable, but is acceptable provided that hybridization to a target nucleotide sequence is sufficiently selective such that it can be distinguished over the non-specific cross-hybridization, for example, at least about 2-fold more selective, generally at least about 3-fold more selective, usually at least about 5-fold more selective, and particularly at least about 10-fold more selective, as determined, for example, by an amount of labeled oligonucleotide that binds to target nucleic acid molecule as compared to a nucleic acid molecule other than the target molecule, particularly a substantially similar (i.e., homologous) nucleic acid molecule other than the target nucleic acid molecule. Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number, if any, of mismatches between the oligonucleotide and sequence to which it is to hybridize.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42EC (moderate stringency conditions); and 0.1×SSC at about 68EC (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

In some embodiments, the biomolecule is an antibody. As used herein, the term "antibody" is used in its broadest sense to include polyclonal and monoclonal antibodies, as well as antigen binding fragments of such antibodies. An antibody useful in a method of the invention, or an antigen binding fragment thereof, is characterized, for example, by having specific binding activity for an epitope of an analyte.

The antibody, for example, includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains. These and other methods of making, for example, chimeric, humanized, CDR-grafted, single chain, and bifunctional antibodies are well known to those skilled in the art.

The term "binds specifically" or "specific binding activity," when used in reference to an antibody means that an interaction of the antibody and a particular epitope has a dissociation constant of at least about $1 \times 10^{-6}$, generally at least about $1 \times 10^{-7}$, usually at least about $1 \times 10^{-8}$, and particularly at least about $1 \times 10^{-9}$ or $1 \times 10^{-10}$ or less. As such, Fab, F(ab')$_2$, Fd and Fv fragments of an antibody that retain specific binding activity for an epitope of an antigen, are included within the definition of an antibody.

In the context of the invention, the term "ligand" denotes a naturally occurring specific binding partner of a receptor, a synthetic specific-binding partner of a receptor, or an appropriate derivative of the natural or synthetic ligands. As one of skill in the art will recognize, a biomolecule (or macromolecular complex) can be both a receptor and a ligand. In general, the binding partner having a smaller molecular weight is referred to as the ligand and the binding partner having a greater molecular weight is referred to as a receptor.

In other embodiments, there are provided methods for detecting an analyte in a sample. Such methods can be performed for example, by contacting a sample containing an analyte with a plurality of surface modified metallic colloids, wherein the analyte binds to the modified metallic surface, and detecting SERS signals emitted by the analyte, wherein the signals are indicative of the presence of the analyte. In this embodiment, the surface of the metallic colloid is modified by attaching an organic molecule to the surface of the colloid, wherein the organic molecule has an affinity for both the metallic surface and the analyte.

By "analyte" is meant any molecule or compound. An analyte can be in the solid, liquid, gaseous or vapor phase. By "gaseous or vapor phase analyte" is meant a molecule or compound that is present, for example, in the headspace of a liquid, in ambient air, in a breath sample, in a gas, or as a contaminant in any of the foregoing. It will be recognized that the physical state of the gas or vapor phase can be changed by pressure, temperature as well as by affecting surface tension of a liquid by the presence of or addition of salts etc.

The analyte can be comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., or an HLA antigen or a microorganism, e.g., bacterium, fungus, protozoan, or virus. In certain aspects of the invention, the analyte is charged.

A member of a specific binding pair ("sbp member") is one of two different molecules, having an area on the surface or in a cavity which specifically binds to and is thereby defined as complementary with a particular spatial and polar organization of the other molecule. The members of the specific binding pair are referred to as ligand and receptor (antiligand) or analyte and probe. Therefore, a probe is a molecule that specifically binds an analyte. These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

Specific binding is the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme—substrate interactions, polynucleotide hybridization interactions, and so forth.

Non-specific binding is non-covalent binding between molecules that is relatively independent of specific surface structures. Non-specific binding may result from several factors including hydrophobic interactions between molecules.

The methods of the present invention may be used to detect the presence of a particular target analyte, for example, a nucleic acid, oligonucleotide, protein, enzyme, antibody or antigen. The methods may also be used to screen bioactive agents, i.e. drug candidates, for binding to a particular target or to detect agents like pollutants.

The polyvalent ligand analytes will normally be poly (amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The monoepitopic ligand analytes will generally be from about 100 to 2,000 molecular weight, more usually from 125 to 1,000 molecular weight. The analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, peptide nucleic acids (PNA), restriction enzymes, activators, repressors, nucleases, polymerases, histones, repair enzymes, chemotherapeutic agents, and the like.

The analyte may be a molecule found directly in a sample such as a body fluid from a host. The sample can be examined directly or may be pretreated to render the analyte more readily detectible. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

In the methods of the invention, a "sample" includes a wide variety of analytes that can be analyzed using the methods described herein, so long as the subject analyte is capable of generating SERS signals upon laser irradiation. For example, a sample can be an environmental sample and includes atmospheric air, ambient air, water, sludge, soil, and the like. In addition, a sample can be a biological sample, including, for example, a subject's breath, saliva, blood, urine, feces, various tissues, and the like.

Commercial applications for the invention methods employing the methods described herein include environmental toxicology and remediation, biomedicine, materials quality control, food and agricultural products monitoring, anaesthetic detection, automobile oil or radiator fluid monitoring, breath alcohol analyzers, hazardous spill identification, explosives detection, fugitive emission identification, medical diagnostics, fish freshness, detection and classification of bacteria and microorganisms both in vitro and in vivo for biomedical uses and medical diagnostic uses, monitoring heavy industrial manufacturing, ambient air monitoring, worker protection, emissions control, product quality testing, leak detection and identification, oil/gas petrochemical applications, combustible gas detection, $H_2S$ monitoring, hazardous leak detection and identification, emergency response and law enforcement applications, illegal substance detection and identification, arson investigation, enclosed space surveying, utility and power applications, emissions monitoring, transformer fault detection, food/beverage/agriculture applications, freshness detection, fruit ripening control, fermentation process monitoring and control applications, flavor composition and identification, product quality and identification, refrigerant and fumigant detection, cosmetic/perfume/fragrance formulation, product quality testing, personal identification, chemical/plastics/pharmaceutical applications, leak detection, solvent recovery effectiveness, perimeter monitoring, product quality testing, hazardous waste site applications, fugitive emission detection and identification, leak detection and identification, perimeter monitoring, transportation, hazardous spill monitoring, refueling operations, shipping container inspection, diesel/gasoline/aviation fuel identification, building/residential natural gas detection, formaldehyde detection, smoke detection, fire detection, automatic ventilation control applications (cooking, smoking, etc.), air intake monitoring, hospital/medical anesthesia & sterilization gas detection, infectious disease detection and breath applications, body fluids analysis, pharmaceutical applications, drug discovery, telesurgery, and the like.

Another application for the sensor-based fluid detection device in engine fluids is an oil/antifreeze monitor, engine diagnostics for air/fuel optimization, diesel fuel quality, volatile organic carbon measurement (VOC), fugitive gases in refineries, food quality, halitosis, soil and water contaminants, air quality monitoring, leak detection, fire safety, chemical weapons identification, use by hazardous material teams, explosive detection, breathalyzers, ethylene oxide detectors and anaesthetics.

In another embodiment, there are provided systems for detecting an analyte in a sample. Such systems include, an array comprising more than one surface modified metallic colloid; a sample containing at least one analyte; a Raman spectrometer; and a computer including an algorithm for analysis of the sample.

A variety of analytical techniques can be used to analyze the samples described herein. Such techniques include for example, nuclear magnetic resonance spectroscopy (NMR), photon correlation spectroscopy (PCS), IR, surface plasma resonance (SPR), XPS, scanning probe microscopy (SPM), SEM, TEM, atomic absorption spectroscopy, elemental analysis, UV-vis, fluorescence spectroscopy, and the like.

In the practice of the present invention, the Raman spectrometer can be part of a detection unit designed to detect and quantify metallic colloids of the present invention by Raman spectroscopy. Methods for detection of Raman labeled analytes, for example nucleotides, using Raman spectroscopy are known in the art. (See, e.g., U.S. Pat. Nos. 5,306,403; 6,002,471; 6,174,677). Variations on surface enhanced Raman spectroscopy (SERS), surface enhanced resonance Raman spectroscopy (SERRS) and coherent anti-Stokes Raman spectroscopy (CARS) have been disclosed.

A non-limiting example of a Raman detection unit is disclosed in U.S. Pat. No. 6,002,471. An excitation beam is generated by either a frequency doubled Nd:YAG laser at 532 nm wavelength or a frequency doubled Ti:sapphire laser at 365 nm wavelength. Pulsed laser beams or continuous laser beams may be used. The excitation beam passes through confocal optics and a microscope objective, and is focused onto the flow path and/or the flow-through cell. The Raman emission light from the labeled silver colloids is collected by the microscope objective and the confocal optics and is coupled to a monochromator for spectral dissociation. The confocal optics includes a combination of dichroic filters, barrier filters, confocal pinholes, lenses, and mirrors for reducing the background signal. Standard full field optics can be used as well as confocal optics. The Raman emission signal is detected by a Raman detector, that includes an avalanche photodiode interfaced with a computer for counting and digitization of the signal.

Another example of a Raman detection unit is disclosed in U.S. Pat. No. 5,306,403, including a Spex Model 1403 double-grating spectrophotometer with a gallium-arsenide photomultiplier tube (RCA Model C31034 or Burle Industries Model C3103402) operated in the single-photon counting mode. The excitation source includes a 514.5 nm line argon-ion laser from SpectraPhysics, Model 166, and a 647.1 mm line of a krypton-ion laser (Innova 70, Coherent).

Alternative excitation sources include a nitrogen laser (Laser Science Inc.) at 337 nm and a helium-cadmium laser (Liconox) at 325 nm (U.S. Pat. No. 6,174,677), a light emitting diode, an Nd:YLF laser, and/or various ions lasers and/or dye lasers. The excitation beam may be spectrally purified with a bandpass filter (Corion) and may be focused on the flow path and/or flow-through cell using a 6× objective lens (Newport, Model L6X). The objective lens may be used to both excite the analyte and to collect the Raman signal, by using a holographic beam splitter (Kaiser Optical Systems, Inc., Model HB 647-26N18) to produce a right-angle geometry for the excitation beam and the emitted Raman signal. A holographic notch filter (Kaiser Optical Systems, Inc.) may be used to reduce Rayleigh scattered radiation. Alternative Raman detectors include an ISA HR-320 spectrograph equipped with a red-enhanced intensified charge-coupled device (RE-ICCD) detection system (Princeton Instruments). Other types of detectors may be used, such as Fourier-transform spectrographs (based on Michaelson interferometers), charged injection devices, photodiode arrays, InGaAs detectors, electron-multiplied CCD, intensified CCD and/or phototransistor arrays.

Any suitable form or configuration of Raman spectroscopy or related techniques known in the art may be used for detection in the methods of the present invention, including but not limited to normal Raman scattering, resonance Raman scattering, surface enhanced Raman scattering, surface enhanced resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

In certain aspects of the invention, a system for detecting an analyte of the present invention includes an information processing system. An exemplary information processing system may incorporate a computer that includes a bus for communicating information and a processor for processing information. In one embodiment of the invention, the processor is selected from the Pentium® family of processors, including without limitation the Pentium® II family, the Pentium® III family and the Pentium® 4 family of processors available from Intel Corp. (Santa Clara, Calif.). In alternative embodiments of the invention, the processor may be a Celeron®, an Itanium®, or a Pentium Xeon® processor (Intel Corp., Santa Clara, Calif.). In various other embodiments of the invention, the processor may be based on Intel® architecture, such as Intel® IA-32 or Intel® IA-64 architecture. Alternatively, other processors may be used. The information processing and control system may further comprise any peripheral devices known in the art, such as memory, display, keyboard and/or other devices.

In particular examples, the detection unit can be operably coupled to the information processing system. Data from the detection unit may be processed by the processor and data stored in memory. Data on emission profiles for various raman labels may also be stored in memory. The processor may compare the emission spectra from the sample in the flow path and/or flow-through cell to identify the ramanactive organic compound. The processor may analyze the data from the detection unit to determine, for example, the sequence of a polynucleotide bound by a silver colloid employed by the methods of the present invention. The information processing system may also perform standard procedures such as subtraction of background signals.

While certain methods of the present invention may be performed under the control of a programmed processor, in alternative embodiments of the invention, the methods may be fully or partially implemented by any programmable or hardcoded logic, such as Field Programmable Gate Arrays (FPGAs), TTL logic, or Application Specific Integrated Circuits (ASICs). Additionally, the disclosed methods may be performed by any combination of programmed general purpose computer components and/or custom hardware components.

Following the data gathering operation, the data will typically be reported to a data analysis operation. To facilitate the analysis operation, the data obtained by the detection unit will typically be analyzed using a digital computer such as that described above. Typically, the computer will be appropriately programmed for receipt and storage of the data from the detection unit as well as for analysis and reporting of the data gathered.

In certain embodiments of the invention, custom designed software packages may be used to analyze the data obtained from the detection unit. In alternative embodiments of the invention, data analysis may be performed, using an information processing system and publicly available software packages.

The invention will be further understood with reference to the following examples, which are purely exemplary, and should not be taken as limiting the true scope of the present invention as described in the claims.

EXAMPLE 1

Preparation of Silver Colloids

A: To a 250 mL round bottom flask equipped with a stirring bar, was added 100 mL de-ionized water and 0.200 mL of a 0.500 M silver nitrate solution. The flask was shaken to thoroughly mix the solution. 0.136 mL of a 0.500 M sodium citrate solution was then added to the flask using a 200 µl pipette. The flask was then placed in a heating mantle and the stirrer was set at medium speed. A water cooled condenser was attached to the flask and heating commenced. The heating mantle was applied at maximum voltage, resulting in boiling of the solution between 7 and 10 minutes. Color changes occur within 120 seconds of boiling. The heating is stopped after 60 minutes, the solution is cooled to room temperature and the resulting colloidal suspension is transferred to a 100 mL glass bottle for storage.

Figure 2:
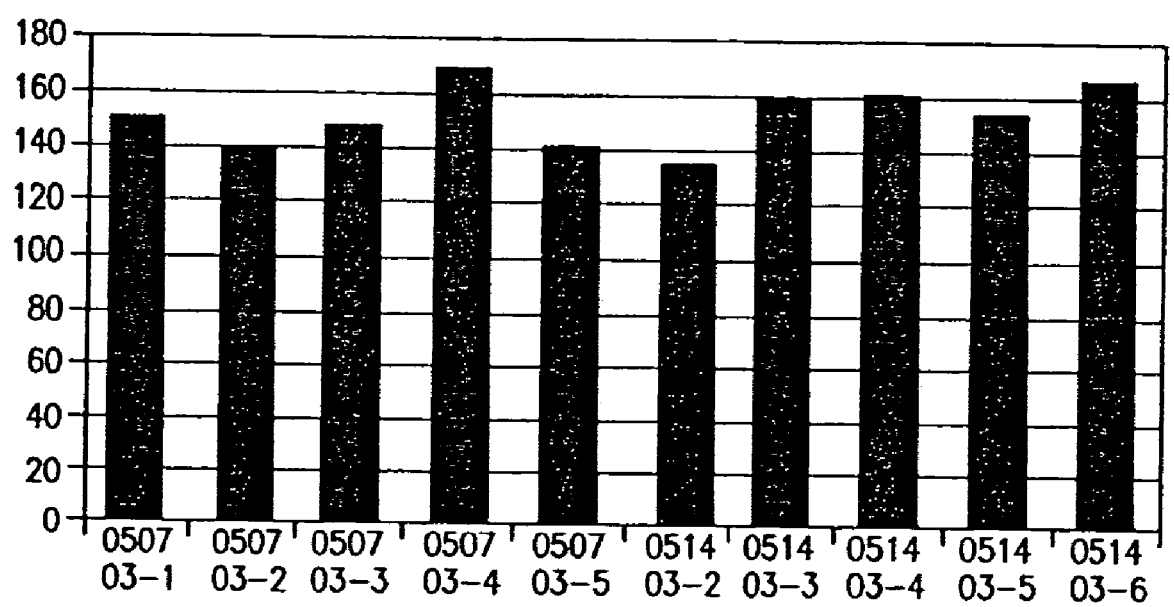
FIG. 2 is a graph illustrating the reproducibility in SERS detection of metallic colloids produced by the methods of the invention.
Figure 3A:
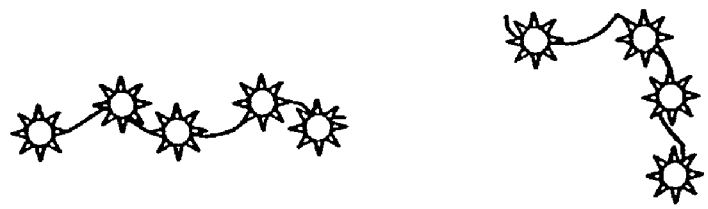
FIG. 3 is a graphical depiction of a biomolecule being adsorbed onto individual metallic colloids produced by the methods of the invention and aggregates thereof.
Figure 3B:
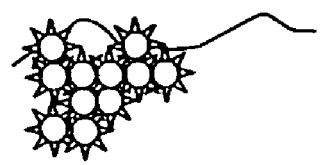
Figure 3C:
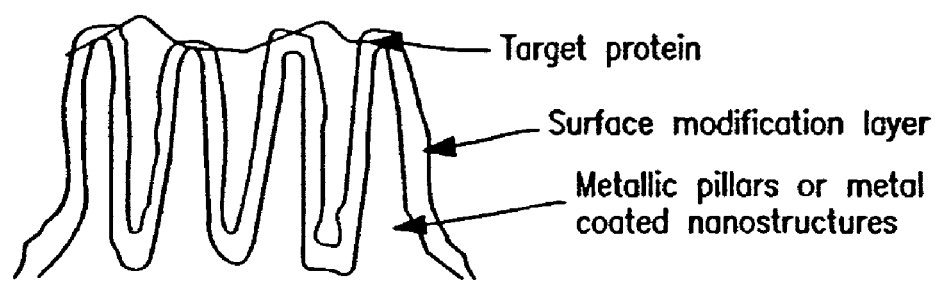

B: To a 250 mL Pyrex glass bottle with 100 mL ultrapure water, was added 1 mL of a 0.500 M silver nitrate solution. This solution was mixed well prior to addition of 0.5 mL of a 0.500M sodium citrate solution. About 3 grams of PTFE boiling stones (6 mm, VWR) were then placed into the bottle. A cap was placed on the bottle but not screwed tightly, and the bottle was placed in the center of a microwave oven (1350 Watt, Panasonic Model NN_S553BF, Type S333). The heating profile was programmed as follows: P10 (maximum power) for 90 seconds and P2 (20% maximum power) for 3:30 minutes. The solution begins to boil in about 60 seconds and color changes occur at 110-120 seconds. After heating the microwave for 5 minutes, the bottle is immediately removed and transferred to a convection oven set at 95° C. (model MO1440SA, Lindberg/Blue, Ashville, N.C.). The bottle is removed from the convection oven and the final volume of the suspension is adjusted to 100 mL with ultrapure water. A typical Raman spectrum is given in FIG. 1. To compare the Raman enhancement with the best lot obtained from a titration method, the peak height at wave number 1320 cm$^{-1}$ was normalized by that of the best lot from the titration method. Data from several preparations using the microwave method are given in FIG. 2.

Although the invention has been described with reference to the above example, it will be understood that modifications and variations are encompassed within the spirit and scope of the invention. Accordingly, the invention is limited only by the following claims.

What is claimed is:

1. A method for producing an aggregate of surface-modified metallic colloid clusters, the clusters comprising metallic particles and at least one Raman-enhancing organic molecule on a surface of the metallic particles, the method comprising:
    a) contacting metal cations with a reducing agent in aqueous solution; and
    b) subsequently heating the aqueous solution, thereby producing metallic colloids;
    c) modifying the metallic colloid cluster by attaching the Raman-enhancing organic molecule to the surface of the metallic colloid cluster to produce the surface-modified metallic colloid, wherein the Raman-enhancing organic molecule comprises a moiety that has an affinity for the metallic colloid and another moiety that has an affinity for a biomolecule; and
    d) aggregating a plurality of the surface-modified metallic colloid to form the cluster of surface-modified metallic colloids.

2. The method of claim 1, further comprising attaching an organic molecule to the surface of the metal colloids.

3. A kit for labeling surface modified metallic colloids comprising a
    plurality of metallic colloids surface modified according to the method of claim 2 and
    a biological agent.

4. The kit of claim 3, wherein the biological agent is a peptide, polypeptide, protein, antibody, or a polynucleotide.

5. The kit of claim 3, wherein the biological agent is a polynucleotide.

6. The kit of claim 3, wherein the biological agent is DNA, RNA or peptide nucleic acid (PNA).

7. The method of claim 1, further comprising the step of boiling the solution.

8. The method of claim 1, wherein the metallic particles comprise a metal selected from the group consisting of silver, gold, platinum, copper, and aluminum.

9. The method of claim 1, wherein the reducing agent is citrate or borohydride.

* * * * *